US009850696B2

(12) United States Patent
Sugaya et al.

(10) Patent No.: US 9,850,696 B2
(45) Date of Patent: Dec. 26, 2017

(54) MICROPARTICLE DETECTION DEVICE AND SECURITY GATE

(71) Applicant: Hitachi, Ltd., Chiyoda-ku, Tokyo (JP)

(72) Inventors: Masakazu Sugaya, Tokyo (JP); Koichi Terada, Tokyo (JP); Hideo Kashima, Tokyo (JP); Yasuaki Takada, Tokyo (JP); Hisashi Nagano, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/402,959

(22) PCT Filed: Apr. 30, 2013

(86) PCT No.: PCT/JP2013/062581
§ 371 (c)(1),
(2) Date: Nov. 21, 2014

(87) PCT Pub. No.: WO2013/175947
PCT Pub. Date: Nov. 28, 2013

(65) Prior Publication Data
US 2015/0136975 A1 May 21, 2015

(30) Foreign Application Priority Data

May 23, 2012 (JP) ................................ 2012-117617

(51) Int. Cl.
*E05F 15/00* (2015.01)
*H01J 49/04* (2006.01)
(Continued)

(52) U.S. Cl.
CPC .............. *E05F 15/40* (2015.01); *E05F 15/72* (2015.01); *E05G 7/00* (2013.01); *E06B 5/10* (2013.01);
(Continued)

(58) Field of Classification Search
CPC ........ E05F 15/40; E05F 15/72; H01J 49/0468
See application file for complete search history.

(56) References Cited

U.S. PATENT DOCUMENTS 5,726,447 A * 3/1998 Aisawa ................. H01J 49/145
250/288
6,295,860 B1 10/2001 Sakairi et al.
(Continued)

FOREIGN PATENT DOCUMENTS

JP 2003-130770 A 5/2003
JP 2004-212073 A 7/2004
(Continued)

OTHER PUBLICATIONS

International Search Report dated Jun. 4, 2013 with English translation (five (5) pages).
(Continued)

*Primary Examiner* — Jason McCormack
*Assistant Examiner* — Sean Luck
(74) *Attorney, Agent, or Firm* — Crowell & Moring LLP

(57) ABSTRACT

In a conventional fine particle detection device that vaporizes fine particles attached to the object of examination by heating, processing capability decreases as the processing time elapses due to the influence of deposition of fine particles other than the object of examination, dirt/dust, a residue of the fine particles as the object of examination, or residual matter. A fine particle detection device according to the present invention includes: a vaporization device that vaporizes the fine particles trapped by a trap device by vaporization or decomposition; a first flow passageway in which a mixture of a component vaporized by the vaporization device and another component flows; a second flow passageway branching from the first flow passageway in a direction of inertial force acting on the other component; a third flow passageway branching from the first flow pas-
(Continued)

sageway in a direction different from the direction of the inertial force; and an analysis device that analyzes a component introduced into the third flow passageway.

16 Claims, 12 Drawing Sheets

(51) Int. Cl.
E05F 15/40 (2015.01)
G01N 1/22 (2006.01)
E05F 15/72 (2015.01)
E05G 7/00 (2006.01)
E06B 5/10 (2006.01)
G01N 1/02 (2006.01)
G01N 33/22 (2006.01)
G01N 15/00 (2006.01)
E05G 5/00 (2006.01)

(52) U.S. Cl.
CPC .......... *G01N 1/2211* (2013.01); *H01J 49/049* (2013.01); *H01J 49/0422* (2013.01); *H01J 49/0459* (2013.01); *H01J 49/0468* (2013.01); *E05G 5/003* (2013.01); *G01N 15/00* (2013.01); *G01N 33/227* (2013.01); *G01N 2001/022* (2013.01)

(56) References Cited

U.S. PATENT DOCUMENTS

| 6,393,894 | B1* | 5/2002 | Bonne | G01N 1/40 |
| | | | | 422/88 |
| 6,884,997 | B2 | 4/2005 | Kashima et al. | |
| 7,275,453 | B2 | 10/2007 | Ishikawa et al. | |
| 8,008,617 | B1* | 8/2011 | Berends, Jr. | H01J 49/0422 |
| | | | | 250/282 |
| 8,560,249 | B2 | 10/2013 | Nagano et al. | |
| 2004/0124352 | A1* | 7/2004 | Kashima | H01J 49/049 |
| | | | | 250/288 |
| 2004/0151543 | A1 | 8/2004 | Mettler et al. | |
| 2005/0279928 | A1* | 12/2005 | Ohkubo | H01J 49/162 |
| | | | | 250/288 |
| 2007/0028670 | A1* | 2/2007 | Bonne | B01L 3/5027 |
| | | | | 73/31.05 |
| 2009/0014638 | A1 | 1/2009 | Itou et al. | |
| 2009/0194687 | A1* | 8/2009 | Jolliffe | H01J 49/24 |
| | | | | 250/288 |
| 2010/0006753 | A1* | 1/2010 | Schroeder | H01J 49/04 |
| | | | | 250/288 |
| 2010/0282961 | A1* | 11/2010 | Miller | G01N 27/624 |
| | | | | 250/282 |
| 2011/0093214 | A1* | 4/2011 | Nagano | G01N 33/227 |
| | | | | 702/24 |
| 2014/0151543 | A1 | 6/2014 | Nagano et al. | |

FOREIGN PATENT DOCUMENTS

| JP | 2005-91118 A | 4/2005 |
| JP | 2005-181098 A | 7/2005 |
| JP | 2006-58318 A | 3/2006 |
| JP | 2007-187467 A | 7/2007 |
| JP | 2011-85484 A | 4/2011 |
| JP | 2011-247609 A | 12/2011 |
| WO | WO 2012/063796 A1 | 5/2012 |

OTHER PUBLICATIONS

Japanese-language Written Opinion (PCT/ISA/237) dated Jun. 4, 2013 (six (6) pages).

* cited by examiner

MICROPARTICLE DETECTION DEVICE AND SECURITY GATE

TECHNICAL FIELD

The present invention relates to a technology for examining fine particles.

BACKGROUND ART

Examples of technology for ensuring safety and security in public facilities, such as airports and seaports, are described in Patent Literatures 1 to 3.

Patent Literature 1 describes a technology for detecting a homemade explosive in a container or attached to a container surface quickly and at low false alarm rate. Specifically, Patent Literature 1 describes performing the steps of suctioning sample gas generated from the container placed on a container table; ionizing the suctioned sample gas using an ion source; subjecting the generated ion to mass analysis; determining the presence or absence of a mass spectrum derived from a homemade explosive on the basis of the mass spectrum obtained by the analysis; and displaying a determination result on a display unit. In paragraph [0022], it is described that fine particles are caused to attach to a fine meshed filter provided in a sample introduction pipe, and the attached fine particles are gasified.

Patent Literature 2 describes a technology where dangerous material, such as represented by a nitro compound, is efficiently ionized using negative corona discharge, and the generated negative ions are detected using a mass spectrometer with high sensitivity. In paragraph [0014], it is described that, in order to prevent the adsorption of gas sample onto the tip portion of a probe, the probe tip is provided with a heater, that a filter is provided to prevent large particles or dust from being directly suctioned into a gas sample introduction pipe, and that a dust outlet is provided for periodic internal cleaning so as to facilitate the removal of dust clogging the filter.

Patent Literature 3 describes a technology for detecting dangerous substance. Specifically, there is described a device including (1) an oven for storing a wiping member to which a sample derived from dangerous material becomes attached, and for heating the sample; (2) a light source that generates an infrared ray for heating the sample from outside the oven; (3) an ion source unit that ionizes the sample vaporized in the oven; (4) an intake pump that introduces the vaporized sample into the ion source unit; (5) a mass analysis unit for ion mass analysis; (6) an exhaust unit; (7) a data processing device that processes an output signal from the mass analysis unit and that determines the presence or absence of dangerous substance; (8) an operation panel that displays a determination result; (9) an alert device that issues an alert based on the determination result; (10) a power supply unit that supplies power to various device units; (11) and a control unit that controls the various device units. In paragraph [0085], it is described that, in order to prevent the entry of foreign matter into the ion source unit, a filter is inserted inside an introduction opening, and that a dirt/dust collecting reservoir portion is provided at the bottom of an insertion portion so as to facilitate removal of collected foreign matter.

CITATION LIST

Patent Literature

Patent Literature 1: JP 2011-85484 A
Patent Literature 2: JP 2006-58318 A
Patent Literature 3: JP 2004-212073 A

SUMMARY OF INVENTION

Technical Problem

In the device installed at public facilities and the like for safety and security purposes, fine particles as the object of examination are often mixed with, or attached to, other fine particles or dust/dirt and the like when trapped, rather than the object fine particles alone being trapped. Thus, the conventional technologies all adopt the configuration in which the flow passageway connected to the analysis device is provided with a filter.

However, as the processing time elapses, fine particles or dirt/dust other than the object of examination, and a residue of the fine particles as the object of examination are deposited and remain in the filter. Namely, filter clogging occurs. Clogging not only causes a decrease in processing capability of the detection device, but also causes contamination, resulting in a decrease in analysis accuracy.

The technology described in Patent Literature 1 presupposes the use of the fine meshed filter for heating the fine particles. Thus, the technology cannot overcome the decrease in processing capability or analysis accuracy described above. In Patent Literature 2 too, there is also the passage mentioning the importance of providing a filter on the flow passageway coupling the probe and the analysis device, indicating that the above problem cannot be overcome, as in the case of Patent Literature 1. The technology according to Patent Literature 3 also requires a filter for preventing the entry of foreign matter into the ion source, so that the above-described problem cannot be solved. Further, in the technology according to Patent Literature 3, the dirt/dust collecting reservoir portion is disposed on the upstream side of the analysis unit. Thus, even if the heating of the dirt/dust collecting reservoir portion can be prevented, cross contamination cannot be eliminated in principle.

In order to overcome these problems, it has been proposed to adopt a structure enabling simple replacement of the filter used for heating the fine particles or for collecting foreign matter. However, even if the proposal is adopted, not only will special equipment be newly required but also the device function will have to be temporarily limited for filter replacement, thus creating new problems with regard to reduction in size of the device or operation of the device.

The conventional filter disposed on the flow passageway for heating fine particles or collecting foreign matter is a planar filter that blocks the entire cross section of the flow passageway in a planar manner. However, a filter of this type of structure is inherently not capable of ensuring large flow passageway conductance, so that it is difficult to ensure processing capability of the device or robustness over a long period of use.

Solution to the Problem

In order to solve the problem, a fine particle detection device according to the present invention includes: a trap device that traps fine particles; a vaporization device that vaporizes the fine particles trapped by the trap device by vaporization or decomposition; a first flow passageway in which a mixture of a component vaporized by the vaporization device and another component flows; a second flow passageway branching from the first flow passageway in a direction of inertial force acting on the other component; a third flow passageway branching from the first flow passageway in a direction different from the direction of the inertial force; and an analysis device that analyzes a component introduced into the third flow passageway.

Advantageous Effects of Invention

According to the present invention, the component obtained by vaporizing the fine particles as the object of examination and the other component (fine particles other than the object of examination, dirt/dust, and a residue of the fine particles as the object of examination that has not been vaporized) can be separated without using a filter. Thus, a fine particles examination device can be realized whereby the decrease in processing capability or degradation in analysis accuracy can be practically avoided regardless of the elapse of the processing time. Other problems, configurations, and effects will become apparent from the following description of embodiments.

DESCRIPTION OF EMBODIMENTS

In the following, embodiments of the present invention will be described with reference to the drawings. The embodiments of the present invention are not limited to the following examples, and various modifications may be made within the scope of the technical concept thereof.

In the following description, the fine particles as the object of detection are explosive fine particles or fine particles attributable to an explosive substance. However, the object of detection is not limited to these fine particles. The fine particles as the object of detection may include a substance having explosibility; stimulant drugs or other drugs; a chemical substance that affects the human body (such as agricultural chemicals); fine particles attributable to a dangerous material and the like generally contemplated to affect the human body; and bacteria, viruses, or other microorganisms that affect the human body.

First Example (Overall Configuration)

Figure 1:
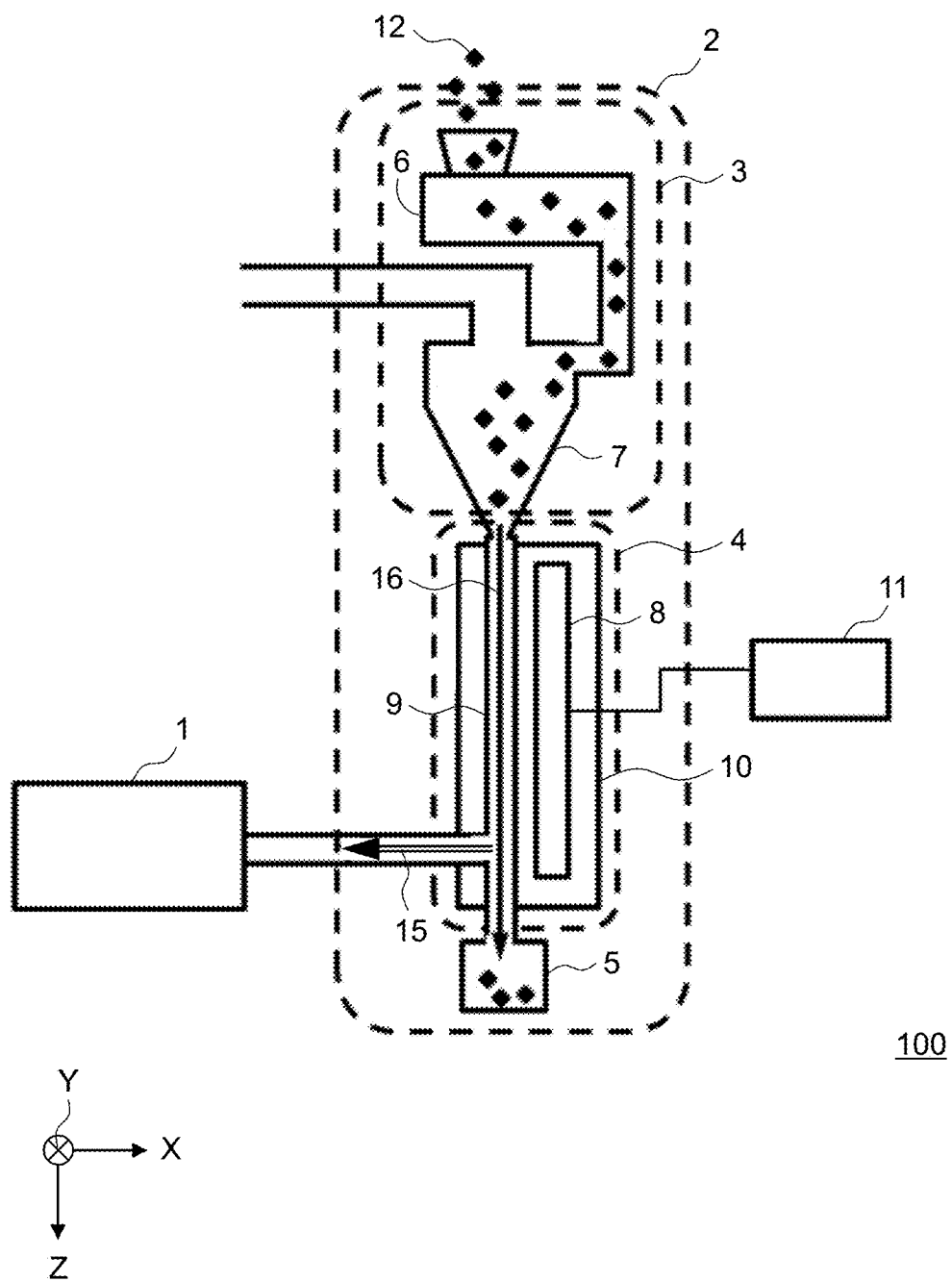
FIG. 1 illustrates a configuration example of a fine particle detection device.

FIG. 1 is a schematic diagram of a fine particle detection device 100 according to an example. The fine particle detection device 100 includes an analysis device 1 and a fine particle processing device 2.

(Analysis Device Configuration)

The analysis device 1 is a device for analyzing vaporized fine particles (a vapor component) and identifying the fine particles. The analysis device 1 may include an ion trap mass spectrometer that utilizes a difference in the mass of substance; an ion mobility mass spectrometer that utilizes a difference in the mobility of ions; a quadrupole mass spectrometer that utilizes the mass-to-charge ratio of fine particles; or a magnetic sector mass spectrometer that utilizes a difference in trajectory when passing a uniform magnetic field. In the fine particle detection device 100 according to the present example, the object of analysis is a vapor component derived from fine particles. Thus, the analysis device 1 contains a vacuum pump and the like capable of negative-pressure suctioning, enabling the suctioning of a vapor component of fine particles as the object of analysis. The analysis device 1 is not necessarily required to be a general-purpose analysis device, and may include a simplified analysis device dedicated for the detection of the vapor component derived from specific fine particles. Generally, reductions in the size or manufacturing cost of the analysis device may be achieved by specializing the device for a particular object of detection.

(Configuration of Fine Particle Processing Device)

The fine particle processing device 2 includes a fine particle trap device 3, a heating vaporization device 4, and a trap 5. The fine particle processing device 2 is coupled with the analysis device 1 via temperature-adjusted piping.

The fine particle trap device 3 is a mechanism or device that traps the fine particles as the object of examination. The present example adopts a mechanism whereby an indirect medium, such as compressed air, is sprayed onto an IC card, a magnetic card, hand baggage, clothing and the like so as to separate and collect fine particles, and then the fine particles containing the object of examination are separated and concentrated using a cyclone centrifugal separator and the like. Alternatively, a system may be adopted wherein an examination medium, such as wiping paper or cloth, is contacted with or rubbed against clothing or hand baggage and the like, and then the fine particles that became attached to the clothing or hand baggage and the like are transferred onto or collected with an examination medium. The fine particle trap device 3 may be provided with any preferred mechanism or configuration depending on the characteristics of the fine particles as the object of examination or the purpose of examination, for example. In FIG. 1, the fine particle trap device 3 including a fine particle collection unit 6 and a cyclone centrifugal separator 7 is illustrated as a representative example. The following description is based on the above device configuration.

The heating vaporization device 4 is a device for vaporizing trapped fine particles. Examples of the vaporizing method include a heating method, and a method by which vaporized fine particle components are separated. The present example adopts a system that vaporizes the trapped fine particles by heating. It should be noted that the fine particles trapped by the fine particle trap device 3 may include not only the fine particles as the object of examination but also fine particles other than the object of examination (such as dust and dirt). The fine particles of an explosive substance as the object of examination may not even be included.

The heating vaporization device 4 illustrated in FIG. 1 includes an infrared lamp 8, a glass pipe 9, and a reflecting mirror 10. The glass pipe 9 is made of a material that transmits infrared ray, and forms a flow passageway through which the fine particles trapped in the fine particle trap device 3 are passed. The reflecting mirror 10 is disposed at the outer periphery of the glass pipe 9 so as to concentrate the infrared ray radiated from the infrared lamp 8 inside the glass pipe 9. In this configuration, the fine particles passing in the glass pipe 9 are partially or entirely vaporized by the radiation heating by the infrared ray radiation. In the following, the elements of the heating vaporization device 4 will be described in greater detail.

The infrared lamp 8 may be configured to emit various wavelengths depending on the material of the contained filament or the temperature thereof, the medium sealed therein, and the like. The infrared lamp 8 according to the example mainly emits infrared radiation including near-infrared ray with wavelengths on the order of 0.8 μm to 2 μm, mid-infrared ray on the order of 2 μm to 5.6 μm, and far-infrared ray on the order of 5.6 μm to 1 mm. The radiation intensity, radiation time and the like of the infrared lamp 8 are controlled by an infrared lamp control device 11. A control program for radiation intensity and radiation time is built inside the infrared lamp control device 11 in advance, for example. Alternatively, the radiation intensity and radiation time of the infrared lamp 8 may be operated remotely.

Depending on the characteristics of the fine particles as the object of examination, an ultraviolet lamp may be used in place of the infrared lamp 8. When an ultraviolet lamp is used, the glass pipe 9 is made of a material that can transmit ultraviolet ray, and the reflecting mirror 10 is made of a material that reflects ultraviolet ray. The ultraviolet lamp herein refers to a lamp having a peak wavelength in an ultraviolet region of from several nm to several hundred nm.

The flow passageway of the glass pipe 9 is branched around the downstream side thereof into two flow passageways. Namely, the glass pipe 9 includes (1) a first flow passageway connected to the fine particle trap device 3 and used for vaporization of fine particles; (2) a second flow passageway for introducing fine particles that have not been vaporized (fine particles other than the object of examination; dust/dirt; and a residue of the fine particles as the object of examination that have not been not vaporized) into the trap 5 (3); and a third flow passageway for introducing the vaporized component into the analysis device 1. In the present example, in the first flow passageway, there exists a mixture of the vaporized component and the non-vaporized component.

The branch direction of the third flow passageway is set in a direction different from the direction of the inertial force acting on the fine particles that have not been vaporized. In the case of FIG. 1, the second flow passageway is in the same direction as the first flow passageway, the direction corresponding to the direction of the inertial force (which is gravitational force in the present case) acting on the fine particles. Meanwhile, the third flow passageway in the case of FIG. 1 is connected in a vertical direction with respect to the first and second flow passageways. The greater the angle at which the third flow passageway is mounted with respect to the second flow passageway, the better; preferably, the angle is from 90° to 180°.

The inertial force acts on the vaporized component as well as on the non-vaporized component. However, because the mass of the vaporized component is small compared with the non-vaporized component, the influence of the inertial force on the vaporized component is small. Thus, the trajectory of the vaporized component can be easily changed compared with the trajectory of the non-vaporized component. Most of the fine particles on which the influence of the inertial force is large and of which the change in trajectory is small (the non-vaporized component) is introduced into the second flow passageway. Some of the fine particles introduced into the second flow passageway collide with the wall surface on the third flow passageway side and are then guided to the trap 5 along the wall surface.

In the case of the present example, it is assumed that the wall surface temperature of at least the flow passageway of the glass pipe 9 coupled with the analysis device 1 (the third flow passageway) is maintained to be approximately equal to or higher than the wall surface temperature of the glass pipe 9 before branching. This is so as to prevent the vapor component generated from the fine particles from becoming adsorbed on the wall surface of the glass pipe 9. On the other hand, the wall surface temperature of the flow passageway of the glass pipe 9 coupled with the trap 5 (the second flow passageway) is maintained to be approximately equal to or lower than the wall surface temperature of the glass pipe 9 before branching. In the present example, the side surface temperature of the second flow passageway is set to be substantially equal to the temperature of the trap 5. This is so as to decrease the likelihood of contamination due to the vapor component being generated from the residue component and the like of the fine particles trapped in the trap 5.

Figure 2:
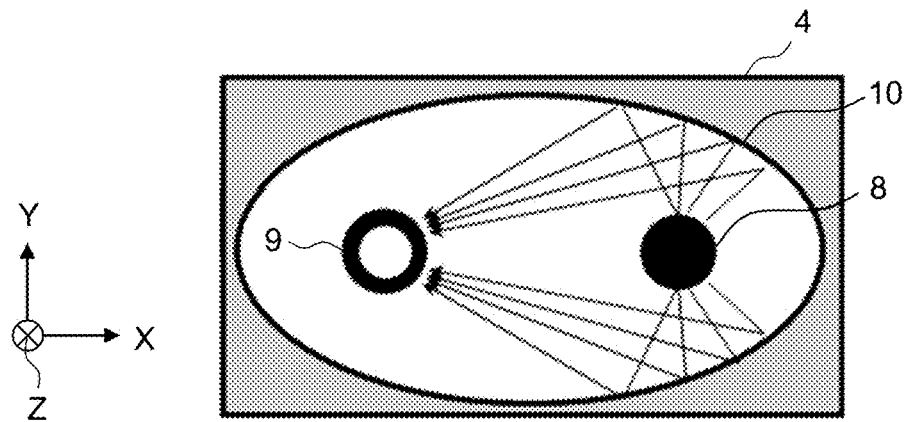
FIG. 2 is a cross sectional view of a heating vaporization device taken vertically with respect to a Z-axis.

FIG. 2 is a cross sectional view of the heating vaporization device 4 taken vertically with respect to the Z-axis. As illustrated in FIG. 2, the reflecting mirror 10 has an elliptical or semi-elliptical shape, or an approximate shape thereof. As illustrated in the figure, the infrared lamp 8 is disposed at one of the two focal points of the reflecting mirror 10, and the glass pipe 9 is disposed at the other point. The arrangement enables the infrared ray radiated from the infrared lamp 8 to efficiently irradiate the fine particles passed inside the glass pipe 9.

(Outline of the Flow from Trapping of Fine Particles to their Detection)

The outline of the processing steps from the trapping of the fine particles to their detection by the fine particle detection device 100 will be described, using explosive material fine particles 12 as an example. In FIG. 1, the fine particles separated from the IC card, hand baggage and the like are transported to the cyclone centrifugal separator 7 via the fine particle collection unit 6. In the cyclone centrifugal separator 7, the explosive material fine particles 12 that have been suctioned together with a large amount of air are separated and concentrated by the principle of centrifugal separation. The explosive material fine particles 12 that have been separated and concentrated are introduced into the glass pipe 9 and then heated by the infrared ray radiated from the infrared lamp 8, whereby some or all of the fine particles 12 are turned into a vapor component. The vapor component and a residue of the fine particles that have not been turned into the vapor are separated at the branch portion of the glass pipe 9 due to the influence of the flow caused by negative-pressure suctioning from the analysis device 1. In FIG. 1, the trajectory of the vapor component is indicated by an arrow 15. The trajectory of the explosive material fine particles 12 that have been separated and concentrated, and the trajectory of the residue of the fine particles that have not been vaporized by the heating vaporization unit 4 are indicated by an arrow 16.

(Separation of Vapor Component and Other Component)

Figure 3:
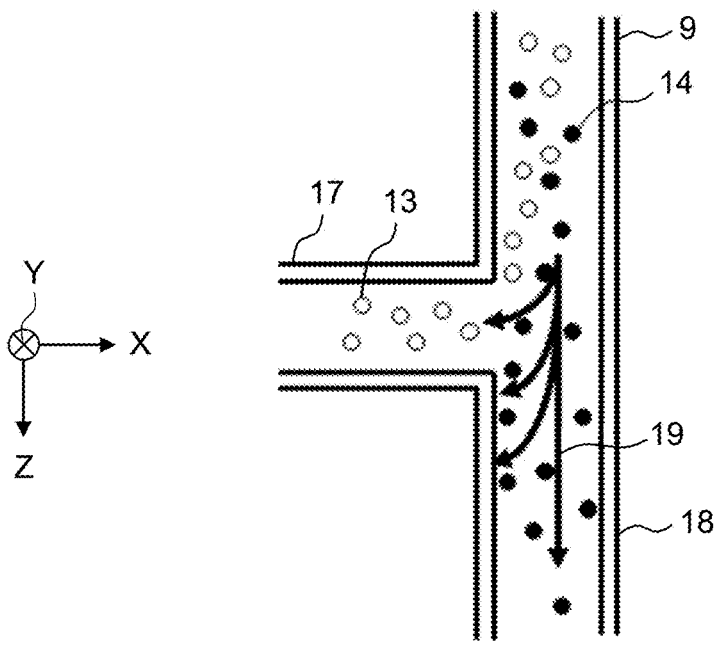
FIG. 3 illustrates a flow passageway branch structure for separating a vapor component from fine particle residue.

With reference to FIG. 3, the separation of the vapor component 13 and the residue 14 of the fine particles that have not been vaporized by the heating vaporization unit 4 at the branch portion of the glass pipe 9 will be described. In FIG. 3, for purpose of description, the vapor component 13 is schematically indicated by white dots, while the fine particle residue 14 is indicated by black dots. In the figure, the Z-axis direction corresponds to the gravitational force direction, and a plane given by the X-axis and the Y-axis corresponds to the horizontal direction.

In FIG. 3, the glass pipe 9 branches into the two different directions of the intake pipe 17 and the branch pipe 18. The glass pipe 9 corresponds to the first flow passageway, the intake pipe 17 corresponds to the third flow passageway, and the branch pipe 18 corresponds to the second flow passageway. The intake pipe 17 is coupled with the analysis device 1, which is not shown in FIG. 3, and the inside of the intake pipe 17 is suctioned by negative pressure. The branch pipe 18 communicates with the trap 5, which is not shown in FIG. 3.

The wall surface temperature of the intake pipe 17 is set to be equal to or higher than the wall surface temperature of the glass pipe 9 before branching, the temperatures being bounded at the branch point. On the other hand, the wall surface temperature of the branch pipe 18 is set to be equal to or lower than the wall surface temperature of the glass pipe 9 before branching, the temperatures being bounded at the branch point. The wall surface temperatures of the intake pipe 17 and the branch pipe 18 may be actively controlled by a pipe heater, an air-cooling fan and the like, or indirectly controlled by ambient temperature.

The vapor component 13 and the fine particle residue 14 passing through the glass pipe 9 travel along trajectories indicated by arrows 19 in the figure due to the influence of a flow moving toward the analysis device 1 via the intake pipe 17, depending on the inertial force acting on the vapor component 13 and the fine particle residue 14. More of the vapor component 13, having a smaller mass and less subject to the influence of the inertial force, is guided in the direction of the intake pipe 17 along the flow. On the other hand, the fine particle residue 14, which has a greater mass and subject to the influence of the inertial force, cannot travel in the direction of the intake pipe 17. Thus, most of the fine particle residue 14 reaches the trap 5 via the branch pipe 18 while colliding with the wall surface of the branch pipe 18, for example.

Further, the wall surface temperatures of the branch pipe 18 and the trap 5 are held lower than the wall surface temperature of the glass pipe 9 before branching. Thus, the fine particle residue 14 introduced into the branch pipe 18 and the trap 5 is subjected to the influence of condensation or adsorption, and do not cause undesirable influence, such as reproducing a vapor component.

As illustrated in FIG. 3, the trajectories of the vapor component 13 and the fine particle residue 14 indicated by the arrows 19 are varied by being subjected to more than a little of the influence of the force of negative-pressure suctioning by the analysis device 1 coupled with the intake pipe 17. The trajectories indicated by the arrows 19 may be adjusted by providing the trap 5 too with a negative-pressure suctioning function so that the negative-pressure suctioning force can be balanced between the intake pipe 17 and the branch pipe 18, whereby the vapor component 13 and the fine particle residue 14 may be separated in a more ideal state.

The magnitude of the suctioning force depends on the explosive substance as the object of detection. For example, in the case of explosive material such as TNT, C4, or RDX, trapping of fine particles on the order of 1 µm to 100 µm (or on the order of 30 µm to 100 µm) is contemplated, where a small, standard type cyclone centrifuge may be used for separation and concentration. For measuring particle size, an electron microscope, sedimentation method, laser diffracted light or scattered light may be used, for example.

The specifications of the infrared lamp 8 for heating the explosive material fine particles depend on the state of trapping of the explosive material fine particles. For example, as the infrared lamp 8, a halogen lamp that generates near-infrared ray with the peak wavelength on the order of 0.8 µm to 2 µm, and that has the electric power density of approximately 3 W/mm is used. Preferably, the temperature of the glass pipe 9 and the intake pipe 17 may be room temperature (20° C.) to approximately 100° C. If the temperature of the glass pipe 9 and the intake pipe 17 is too high, the vapor component derived from the explosive material may be dissolved and eliminated.

The wall surface temperature of the trap 5 and the branch pipe 18 may be equal to or less than the temperature of the glass pipe 9 and the intake pipe 17. In the present example, the temperature of the trap 5 disposed at the distal end of the branch pipe 18 is room temperature, while the wall surface temperature of the branch pipe 16 is provided with a temperature gradient starting from the branch point. Preferably, the flow rate in the intake pipe 15 due to the negative-pressure suctioning by the analysis device 1 may be approximately 0.5 to 2 L/min. The amount suctioned in the direction of the trap 5 depends on the conductance of the intake pipe 17 and the branch pipe 18; preferably, the amount suctioned may be on the order of 0 to 10 L/min. When the amount suctioned in the direction of the trap 5 is 0 L/min, the residue 14 in the branch pipe 18 moves by falling due to the force of gravity. Thus, the extended direction of the branch pipe 18 is limited to the direction of gravitational force. When the amount suctioned in the direction of the trap 5 is not 0 L/min, the residue 14 is moved by the suctioning force, so that there are no restrictions as to the direction in which the branch pipe 18 is disposed, for example.

In the foregoing description, the vapor component 13 is generated from the explosive material fine particles 12 using an infrared ray heating system. However, depending on the composition of the explosive material fine particles 12, a gas component corresponding to the vapor component 13 may be obtained by decomposition of the explosive material fine particles 12 by ultraviolet ray irradiation. When ultraviolet ray is used too, the presence or absence of the explosive material fine particles 12 and the identity of components can be efficiently analyzed through the same steps as in the above-described mechanism.

Effects of the Example

As described above, the fine particle detection device 100 according to the present example generates the vapor component 13 required for analysis from the material fine particles 12 by non-contact heating using infrared ray. This prevents the deposition or a residue of fine particles or dust/dirt on the heating member, and the resultant clogging of the flow passageway, which may be caused in the case of contact heating as the processing time elapses. Accordingly, the fine particle detection device 100 according to the present example is not subject to a decrease in processing capability attributable to the deposition or a residue of fine particles or dust/dirt, or to degradation of analysis accuracy due to contamination.

Further, in the fine particle detection device 100 according to the present example, the vapor component 13 attributable to the explosive material fine particles 12 is generated by non-contact heating in the glass pipe 9, i.e., in a state isolated from the surrounding environment, and then guided to the intake pipe 17. Thus, the vapor component 13 is not prone to the influence of the heating member or the surrounding environment, whereby the analysis accuracy can be increased.

In the fine particle detection device 100 according to the present example, there is no need for using a heating filter and the like to obtain the vapor component 13. Thus, the structure for obtaining the vapor component 13 is simplified compared with conventional technology. The fine particle detection device 100 according to the present example is not only easy to maintain compared with conventional technology, but also minimizes operational restrictions, such as temporarily stopping or limiting the device function for maintenance, enabling maintenance of device performance over a long period.

The infrared lamp 8 used for obtaining the vapor component 13 can modify its heating condition at high speed. Thus, the time required for rising to the process temperature, or the time required for falling from the process temperature can be decreased. When the infrared lamp 8 is used, there is no need for preliminary heating during stand-by. When a halogen lamp heater that radiates mainly near-infrared ray is used as the infrared lamp 8, rising or falling is possible within several seconds. Thus, unwanted power consumption can be decreased.

When the infrared lamp 8 is used as in the present example, the heating condition can be modified at high speed. Thus, a complex heating program can be implemented. For example, the heating condition can be modified to a preferred heating condition in a short time depending on the composition of the fine particles as the object of detection. A precise temperature control can also be implemented.

Second Example

An example will be described in which the fine particle detection device 100 is applied in a security gate 41 equipped with an IC card authentication function.

Figure 4:
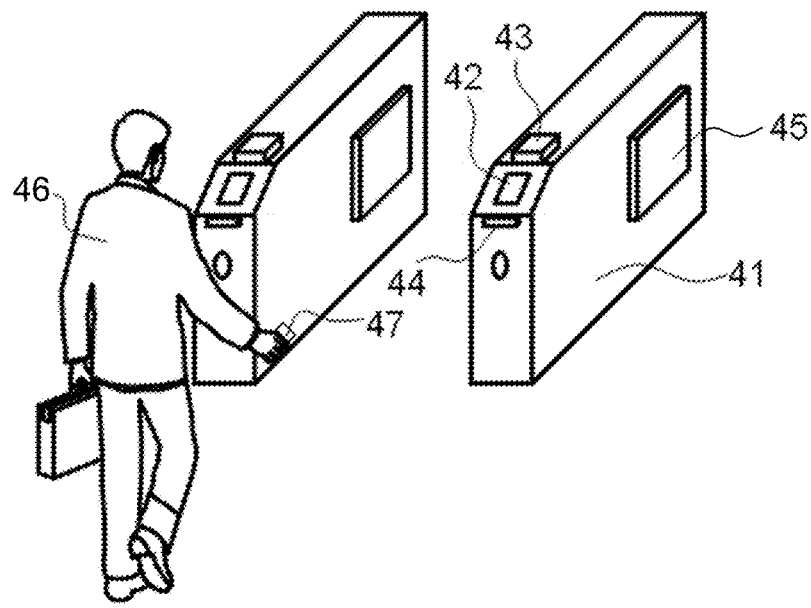
FIG. 4 illustrates an example of the exterior view of a security gate.

FIG. 4 is an exterior configuration example of a security gate 41 of at-hand suction type. The security gate 41 includes a card reader 42 for reading ID information from a medium such as an ID card 47; a separating mechanism 43 for separating explosive material fine particles or the like attached to the IC card 47 or the like; a trap device 44 for trapping the separated explosive material fine particles or the like; and an open/close gate 45. In FIG. 4, the case is contemplated in which the object of examination 46 is a person, who passes the security gate 41 after authentication using the ID card 47.

Figure 5:
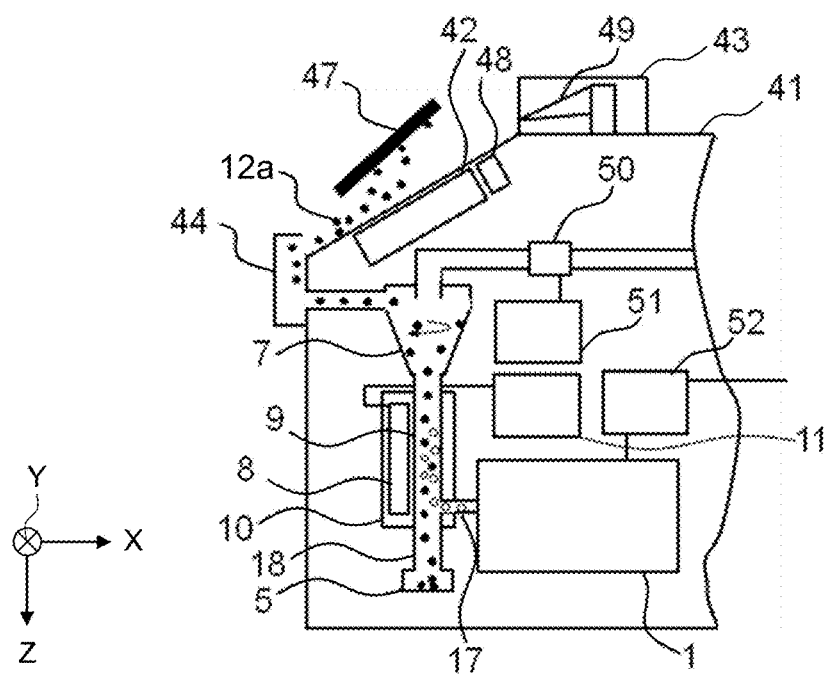
FIG. 5 illustrates a cross-sectional configuration example of the security gate.
Figure 6:
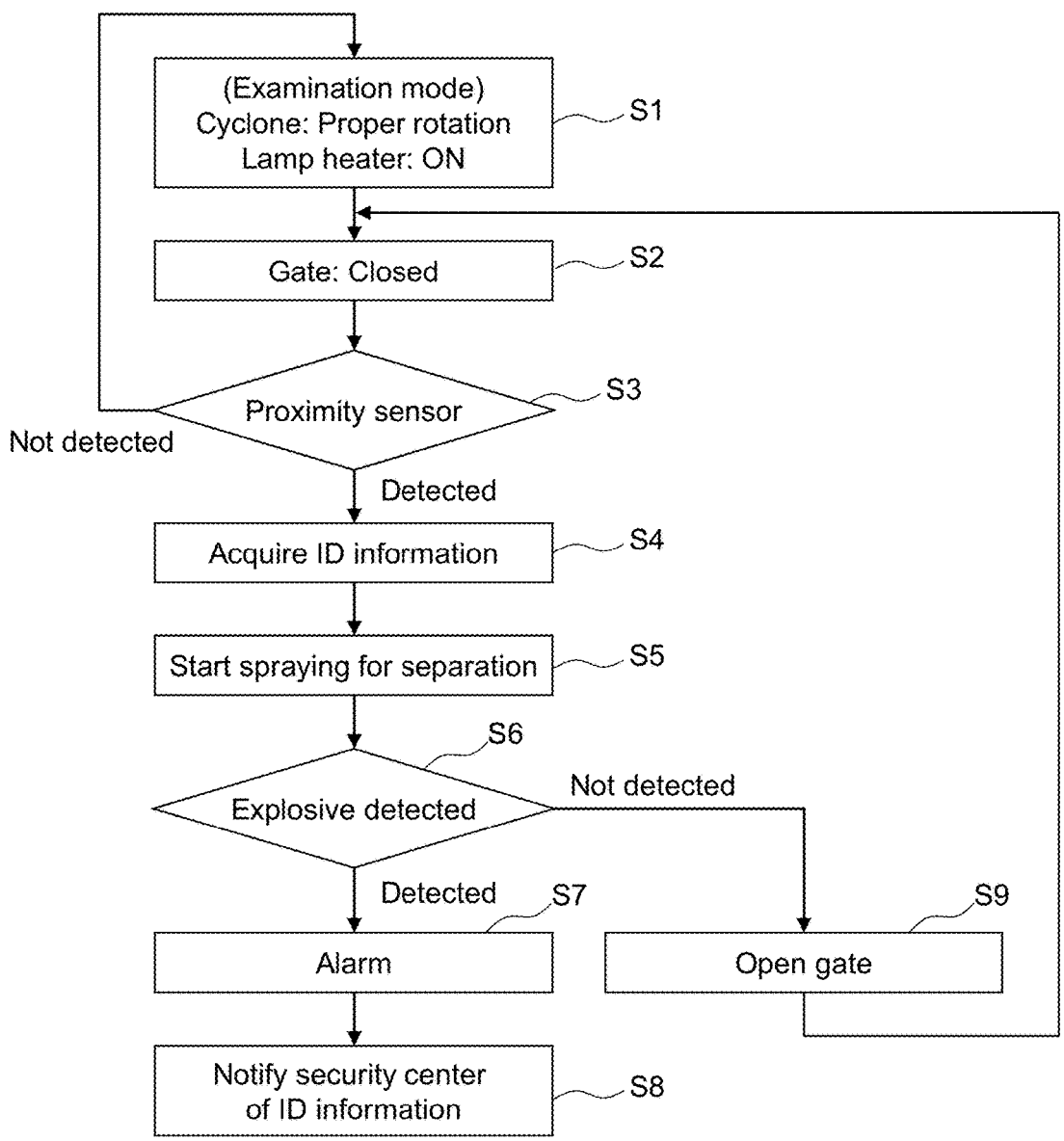
FIG. 6 is a flowchart of an operation sequence of the security gate.

FIG. 5 is a partially cutaway view of the security gate 41. In FIG. 5, the internal configuration of the security gate 41 including the fine particle detection device 100 (FIG. 1) is illustrated. FIG. 6 is a flowchart of an operation sequence of the security gate 41.

The security gate 41 repeatedly executes the process of steps S1 to S3 until the proximity of the ID card 47 to the card reader 42 is detected. Specifically, in step S1, a fan control device 51 controls the rotation speed of a cyclone generated in the centrifugal separator 7 in a proper range. The infrared lamp control device 11 also controls the infrared lamp 8 to a lighted state. In step S2, a detection control device 52 controls the open/close gate 45 to a closed state. In step S3, a proximity sensor 48 detects the presence or absence of proximity of the ID card 47 to the card reader 42. The proximity sensor 48 is disposed in the vicinity of the ID card 47.

When the person as the object of examination 46 brings the ID card 47 close to the card reader 42, the proximity sensor 48 detects the approach. Upon notified of the approach of the ID card 47, the card reader 42 acquires ID information from the ID card 47 in a non-contact manner (step S4). When the ID card 47 is recorded as magnetic information, a magnetic head may be contacted so as to read the ID information. In the case of the present example, after the ID information is read, a pulsed compressed air is sprayed for a certain time from a compressed air spray nozzle 49 installed in the separating mechanism 43 under the control of a control unit, which is not illustrated (step S5). The compressed air is jetted so as to separate the fine particles attached to the surface of the approaching ID card 47 using an air flow. In the case of the present example, the spray pressure is 0.05 MPa to 0.1 MPa. The compressed air is sprayed toward the ID card 47 at the frequency on the order of 1 to 5 times per second.

The explosive material fine particles 12*a* or other fine particles (the explosive material fine particles 12*a* may not be included) separated from the surface of the ID card 47 are transported to the cyclone centrifuge 7 via the trap device 44. The fine particles are transported to the cyclone centrifuge 7 by the suctioning force generated by an axial-flow fan 50 controlled by the fan control device 51. As described above, the fine particles transported to the cyclone centrifuge 7 are separated and concentrated and then introduced into the glass pipe 9, where the fine particles are vaporized by heating by the infrared lamp 8, forming the vapor component. The vapor component 13 is further introduced into the analysis device 1 via the intake pipe 17 to analyze their compositional substances. An analysis result from the analysis device 1 is fed to the detection control device 52 and compared with the component data of a specific explosive substance. The detection control device 52 determines whether, based on the result of the comparison, the substance of the vapor component 13 is an explosive substance to be detected (step S6).

When the explosive substance to be detected is detected, the detection control device 52 issues an alarm (step S7), and notifies a security center of the ID information and the like of the ID card 47 (step S8). On the other hand, when the explosive material to be detected is not detected, the detection control device 52 opens the open/close gate 45 to permit the passage of the object of examination 46 (step S9). After step S9, the detection control device 52 returns to the process of step S2 and controls the open/close gate 45 to closed state in preparation for the passage of the next object of detection 46.

The above-described security gate 41 may be applied for entry/exit management at public facilities, such as an airport, a seaport, a station ticket gate, a commercial facility, an office building, or an amusement facility. For example, the above-described conditions may be combined to implement detection of an explosive material, such as TNT, at the rate of several seconds or less per person.

Third Example

Figure 7:
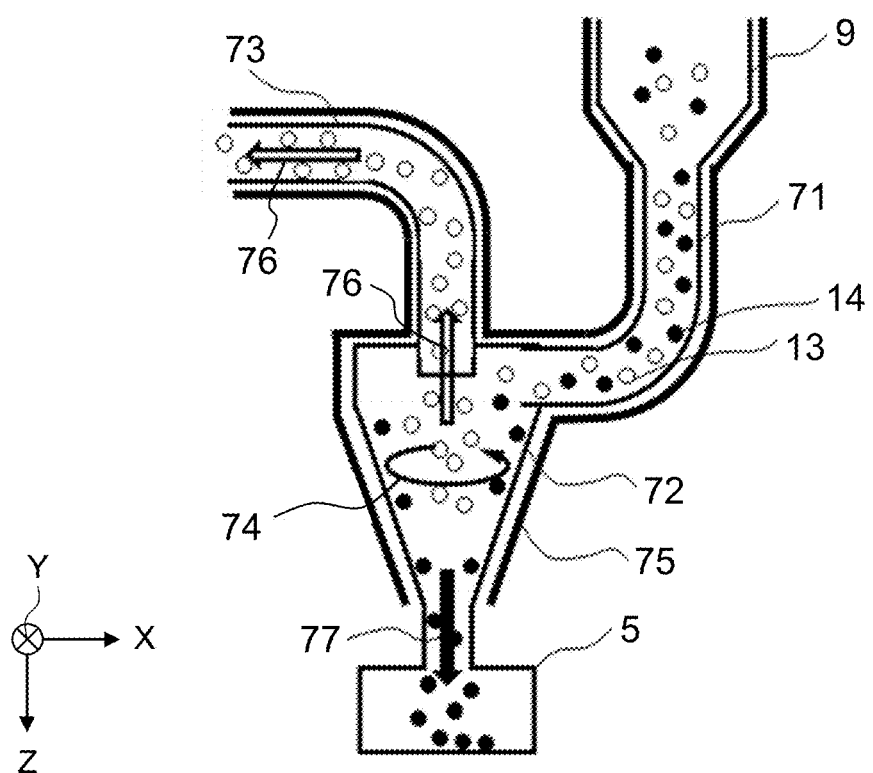
FIG. 7 illustrates a mechanism for separating the vapor component from fine particle residue using centrifugal force.

Another configuration example of the fine particle detection device 100 will be described. In the present example, a preferred configuration for separation of the vapor component 13 and the fine particle residue 14 will be described. FIG. 7 illustrates a constituent portion specific to the present example. The present configuration is similar to the configuration of the fine particle detection device 100 illustrated in FIG. 1 described with reference to the first example, with the exception of the mechanism for separating the vapor component 13 and the fine particle residue 14. Thus, description of the configuration of portions common to FIG. 1 will be omitted.

As illustrated in FIG. 7, in the case of the present example, a cyclone separation system is applied, instead of the simple branch structure of the glass pipe 9 illustrated in FIG. 3. Namely, in the present example, centrifugal force is utilized to enable more efficient separation of the vapor component 13 and the fine particle residue 14. In FIG. 7 too, as in the case of description with reference to FIG. 3, the vapor component 13 is schematically indicated by white dots, and the fine particle residue 14 is indicated by black dots.

As illustrated in FIG. 7, the vapor component 13 and the fine particle residue 14 are introduced into a centrifugal separator 72 via a coupling pipe 71 coupled with the lower end portion of the glass pipe 9. One end of the coupling pipe 71 is coupled with the side of an upper surface portion of the centrifugal separator 72, which has a cylindrical shape. At the center of the upper surface of the centrifugal separator 72, an intake pipe 73 is coupled. The other end of the intake pipe 73 is coupled with the analysis device 1 having the negative-pressure suctioning function. Thus, in the centrifugal separator 72, a rotating air flow is generated by the negative-pressure suctioning by the analysis device 1 in the direction indicated by an arrow 74. Namely, the so-called cyclone phenomenon is produced in the centrifugal separator 71. The rotating air flow will be described. The air flow that has flown via the coupling pipe 71 into the centrifugal separator 72 at around the upper surface thereof descends while rotating along the inner wall of the cylindrical portion. The descent here is due to the gravitational force. The air flow eventually reaches a conical portion formed at the lower end side of the centrifugal separator 72. In the conical portion, because the radius of rotation becomes smaller, the air flow increases speed as it descends according to the principle of constant rotational momentum. At this time, the pressure at around the center of the centrifugal separator 72 is decreased by the influence of the centrifugal force. Thus, as the air flow nears the lower end of the conical portion (i.e., as the air flow approaches the trap 5), the air flow at around the center of the centrifugal separator 72 is inverted upward and exhausted into the intake pipe 73.

In the following, a case will be considered in which the vapor component 13 and the fine particle residue 14 are introduced into the centrifugal separator 72 where such rotating air flow is generated. In this case, due to the centrifugal force by the rotating air flow, the fine particle residue 14 with a relatively large mass is separated outward and then falls along the inner wall of the conical portion into the trap 5 where the residue is collected. On the other hand, the vapor component 13 with a relatively small mass is less prone to the influence of centrifugal force. Thus, the vapor component 13 is introduced into the intake pipe 73 together with the ascending air flow, and eventually transported into the analysis device 1. In the figure, an arrow 76 indicates the direction of movement of the vapor component 13, and an arrow 77 schematically indicates the direction of movement of the fine particle residue 14.

In order to cause the rotating air flow for separating the vapor component 13 and the fine particle residue 14 in the centrifugal separator 72, the air flow at the entry of the centrifugal separator 72 needs to have a certain flow velocity or higher. The flow velocity is subject to the influence of the shape (size) of the centrifugal separator 72 or the roughness of the inner wall surface thereof; preferably, the flow velocity may be approximately 10 m/sec. For example, when the flow rate of the negative-pressure suctioning by the analysis device 1 coupled with the intake pipe 73 is on the order of 0.6 to 2 L/min, in order to obtain the entry flow velocity of approximately 10 msec, it is preferable that the diameter of the coupling pipe 71 or the entry diameter of the centrifugal separator 72 is on the order of 1 to 2 mm.

In the case of the present cyclone separation system, the vapor component 13 and the fine particle residue 14 often contact the wall surfaces of the coupling pipe 71, the centrifugal separator 72, and the intake pipe 73. If the temperature of these wall surfaces is low, condensation of the vapor component 13 or the fine particle residue 14 may be caused on the wall surfaces. Thus, in the present example, in order to prevent condensation of the vapor component 13 or the fine particle residue 14 on the wall surfaces, a wall surface heater 75 is disposed along the wall surfaces. While a preferable temperature of the wall surfaces depends on the explosive material component as the object of detection, it is preferable to adjust the temperature between room temperature (20° C.) and approximately 100° C.

Fourth Example

Figure 8:
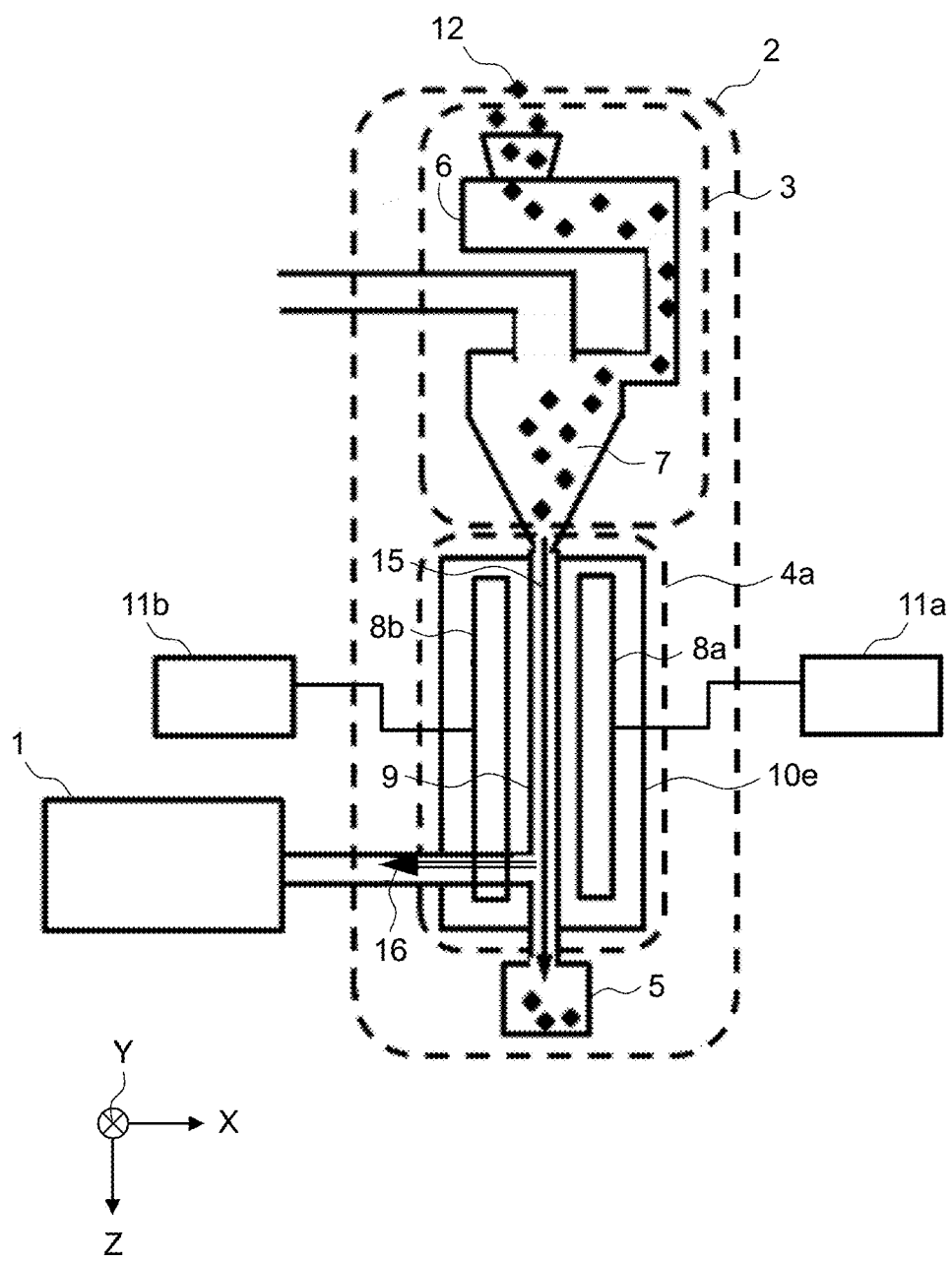
FIG. 8 illustrates another configuration example of the fine particle detection device.

Another configuration example of the fine particle detection device 100 will be described. In the present example, a case will be described in which a configuration example of the heating vaporization device different from that of the fine particle detection device 100 according to the first example is adopted. FIG. 8 illustrates the configuration example of the fine particle detection device 100 according to the present example. In FIG. 8, portions corresponding to those of FIG. 1 are designated with the identical or corresponding signs. The constituent portion unique to FIG. 8 is a heating vaporization device 4a. The heating vaporization device 4a includes four infrared lamps 8a, 8b, 8c, and 8d (of which 8c and 8d are not shown), and a reflecting mirror 10e (formed of four reflecting mirrors 10a, 10b, 10c, and 10d), which are controlled by infrared lamp control devices 11a, 11b, 11c, and 11d (of which 11c and 11d are not shown).

Namely, the present example uses four infrared lamps 8a, 8b, 8c, and 8d which are disposed around the glass pipe 9 so as to heat the explosive material fine particles 12 passing in the glass pipe 9. The four infrared lamp control devices 11a, 11b, 11c, and 11d respectively corresponding to the four infrared lamps 8a, 8b, 8c, and 8d control the radiation intensity, radiation time and the like of the respectively corresponding infrared lamps. As in the case of the first example, radiation intensity, radiation time and the like may be controlled by a program contained in the infrared lamp control device in advance, or may be operated remotely. The four infrared lamps may have independent control conditions, or two or more of the infrared lamps may be operatively linked.

Figure 9:
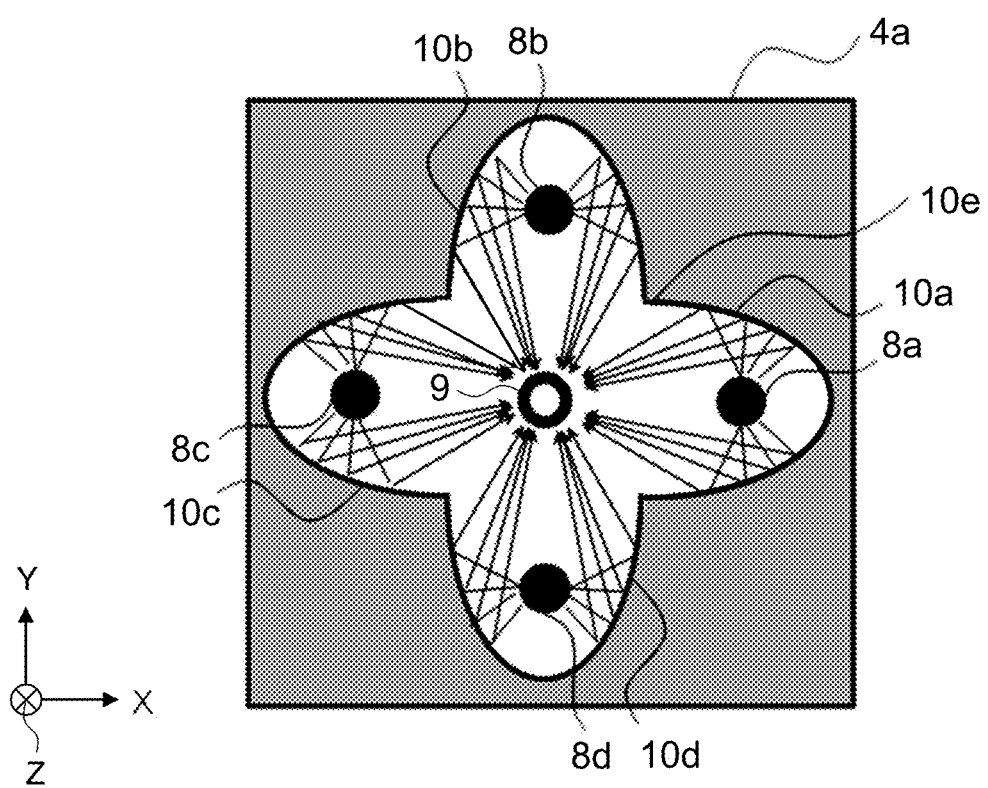
FIG. 9 is a cross sectional view of the heating vaporization device taken vertically with respect to the Z-axis.

FIG. 9 is a cross sectional view of the heating vaporization device 4a adopted in the present example taken vertically with respect to the Z-axis. As illustrated in FIG. 9, the four infrared lamps 8a, 8b, 8c, and 8d are disposed around the single glass pipe 9 at four locations. The reflecting mirror 10e includes the four reflecting mirrors 10a, 10b, 10c, and 10d having an elliptical or semi-elliptical shape, or an approximate shape thereof, which are coupled with each other and disposed such that, of the two focal points of each of the four reflecting mirrors 10a, 10b, 10c, and 10d, one is redundant. At the redundant position of the focal points of the four reflecting mirrors 10a, 10b, 10c, and 10d, the glass pipe 9 is disposed. At the focal points of the four reflecting mirrors 10a, 10b, 10c, and 10d that are not redundant, the infrared lamps 8a, 8b, 8c, and 8d are respectively disposed. In this configuration, the infrared rays radiated from the four infrared lamps 8a, 8b, 8c, and 8d can be efficiently condensed as the infrared rays irradiate the explosive material fine particles 12 passing in the glass pipe 9.

By adopting the heating vaporization device 4a of the above-described configuration in the fine particle detection device 100 according to the present example, functional enhancement can be provided as will be described below, in addition to the functions of the previously described examples.

First, in the case of the present example, the amount of irradiation of infrared ray for obtaining the vapor component from the fine particles as the object of examination can be increased. When the fine particles as the object of detection is a material having a low rate of absorption with respect to the wavelength range of the infrared lamp, or when the light-receiving area of the fine particles themselves is small, it is necessary to increase the output of the infrared lamp. Generally, in order to increase the infrared lamp output, there may be adopted the method that uses an infrared lamp having higher electric power density, or the method where an infrared lamp having a longer infrared ray emitting portion is used to extend the heated flow passageway. However, the former method may newly require a water-cooling mechanism for protecting the infrared lamp, or a new countermeasure including consideration of heat dissipation to surrounding areas, for example. The latter method is disadvantageous for decreasing the size of the infrared lamp, and, as a result, for decreasing the size of the fine particle detection device 100. In the latter method, depending on the fine particles as the object, vaporization by heating may be difficult.

On the other hand, when the four infrared lamps 8a, 8b, 8c, and 8d are used as in the present example, even though the performance of the individual infrared lamp is the same as that of the infrared lamp of the first example, the amount of irradiation of the infrared ray with which the fine particles passing inside the glass pipe 9 can be irradiated can be increased by a maximum of four times.

Secondly, in the case of the present example, the operating life of the infrared lamps 8a, 8b, 8c, and 8d can be extended compared with the first example. In an infrared lamp, particularly a halogen lamp, when the output voltage is decreased by 10%, the operating life can be extended by approximately three times. Thus, if a halogen lamp operating at the rate output of 100% were to be modified for operation at 70% of the rated output, its operating life can be extended by approximately 3000 times, which is a significant improvement in maintainability. When the amount of irradiation of infrared ray in the present example is the same as the amount of irradiation in the case of the first example, for example, the output of each infrared lamp becomes one fourth, enabling a significant increase in operating life.

Thirdly, in the case of the present example, the four infrared lamps 8a, 8b, 8c, and 8d can emit wavelengths in two or more wavelength ranges simultaneously. When the fine particles as the object of detection can be irradiated with infrared ray or ultraviolet ray in a plurality of different wavelength ranges, multiple kinds of fine particles can be simultaneously vaporized by heating. Actually, there are cases where the wavelength range of the infrared lamp with which the fine particles as the object of detection should be irradiated for vaporization by heating cannot be predicted, or where it is desired to heat and vaporize a plurality of fine particles simultaneously that have different suitable wavelength ranges of the infrared lamp for vaporization by heating.

In the present example, the infrared lamps 8a, 8b, 8c, and 8d may include infrared lamps and/or ultraviolet lamps that radiate different wavelength ranges of infrared ray and/or ultraviolet ray. For example, the infrared lamp 8a may be an infrared lamp that emits near-infrared ray of wavelengths on the order of 0.8 µm to 2 µm; the infrared lamp 8b may be an infrared lamp that emits mid-infrared ray of wavelengths on the order of 2 µm to 5.6 µm; the infrared lamp 8c may be an infrared lamp that emits far-infrared ray of wavelengths on the order of 5.6 µm to 1 mm; and the infrared lamp 8d may be an ultraviolet lamp that emits wavelengths shorter than 100 nm. In this configuration, the fine particles can be vaporized by heating or decomposed in a wide range of wavelengths from the ultraviolet region to the far-infrared region, in order to obtain the vapor component. According to conventional technology, implementation of such a plurality of heating conditions is difficult in principle.

Fourth, in the present example, the size of the heating vaporization device 4a in the lamp length direction thereof can be decreased. In order to realize a security gate or a small, portable fine particle detection device, it is necessary to reduce the size of the constituent elements of the device. In the present example, when the same amount of irradiation as in the first example is irradiated onto the glass pipe 9, the length of the infrared lamps 8a, 8b, 8c, and 8d can be made one fourth the infrared lamp 8 of the first example. Thus, the size of the heating vaporization device 4a can be significantly reduced in the lamp length direction compared with the heating vaporization device 4 according to the first example.

In the present example, the case has been described in which the number of the lamps in the heating vaporization device 4a is four. However, the number of the lamps is not limited to four. The number of the lamps in the heating vaporization device 4a may be two, three, or four or more. Similarly, the number of the coupled reflecting mirrors in the reflecting mirror 10e with the elliptical or semi-elliptical shape or an approximate shape thereof may be any number.

Fifth Example

Figure 10:
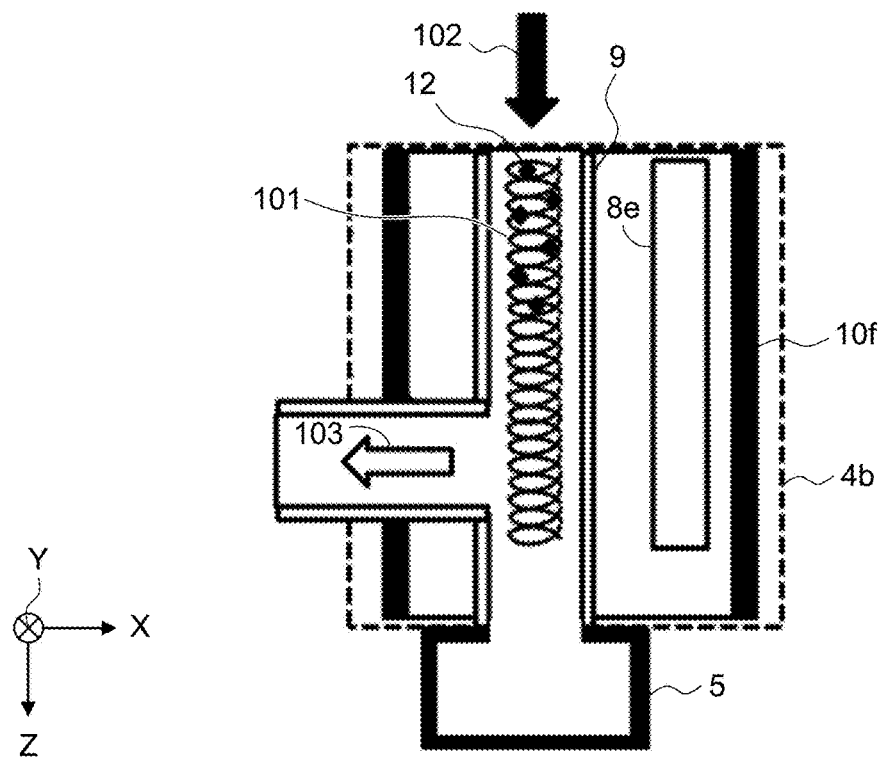
FIG. 10 illustrates another configuration example of the heating vaporization unit which may be preferably used in the fine particle detection device.

Another configuration example of the fine particle detection device 100 will be described. In the present example, a case in which the heating vaporization device of a different structure from that of the first example is adopted will be described. The configuration of the fine particle detection device 100 according to the present example is similar to the first example with the exception of the heating vaporization device. FIG. 10 illustrates the configuration example of a heating vaporization device 4b used in the present example. In FIG. 10, portions corresponding to those of FIG. 1 are designated with the same or corresponding signs.

In the heating vaporization device 4b according to the present example too, the tip of the glass pipe 9 is branched into the intake pipe 17 and the branch pipe 18. The difference lies in that a trap wire 101 of a three-dimensional structure is provided in the glass pipe 9 in the flow passageway direction. The present example is also similar to the first example in that the glass pipe 9 is disposed at one of the focal points of a reflecting mirror 10f having an elliptical or semi-elliptical shape or an approximate shape thereof, while an infrared lamp 8e is disposed at the other focal point of the reflecting mirror 10f.

In the following, the trap wire 101, which is a structural member unique to the present example and which functions as an obstacle with respect to the fine particles will be described. The trap wire 101 is made of a spiral coil extending in the direction of the flow passageway direction of the fine particles (the axial direction of the glass pipe 9), for example. A conventional planar mesh filter has its filter plane disposed such that the flow passageway cross section is entirely blocked. In this respect, the structure of the trap wire 101 is clearly different from the conventional filter.

The explosive material fine particles 12 introduced from the fine particle trap device 3 into the glass pipe 9 and passing therein moves with Brownian motion. Thus, during the propagation inside the glass pipe 9, the explosive material fine particles 12 contact the trap wire 101 or become temporarily attached thereto. The explosive material fine particles 12, as they pass inside the glass pipe 9 or as they contact or become attached to the trap wire 101, are heated by the infrared ray condensed by the reflecting mirror 10f. As a result, the particles are partially or entirely vaporized, forming the vapor component 13.

The vapor component 13 generated in the glass pipe 9 is guided to the analysis device 1 (not illustrated) via the intake pipe 17 as described in the first example, where it is determined whether the vapor component 13 is an explosive substance to be detected. In FIG. 10, the direction of entry of the explosive material fine particles 12 is indicated by an arrow 102, and the direction of flow of the vapor component 13 is indicated by an arrow 103.

In FIG. 10, the spiral coil structure has been described as an example of the trap wire 101. However, the shape of the trap wire 101 is not necessarily limited to the spiral coil structure. As long as the same effect can be obtained, the structure need not even be regular or periodic with respect to the flow passageway direction.

Figure 11:
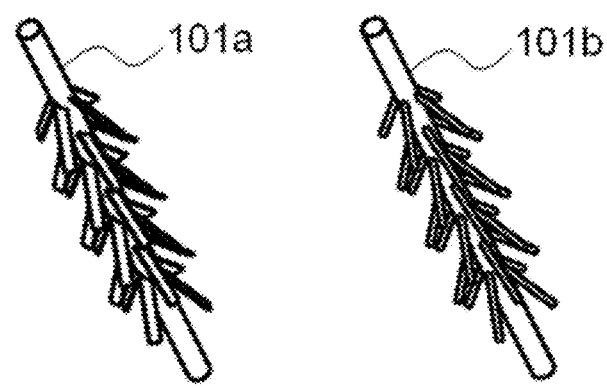
FIG. 11 illustrates shape examples of a trap wire.

FIG. 11 illustrates other structure examples of the trap wire having a three-dimensional structure in the flow passageway direction. In trap wires 101a and 101b, a thin column extending in the flow passageway direction is formed with fin-shaped protrusions or bar-shaped protrusions, for example. Preferably, the protrusions are extended in the direction of flow of gas so as not to interfere with the flow in the glass pipe 9. The protrusions may or may not be disposed regularly or periodically with respect to the axial direction of the column. However, care must be taken as to the density or gap of the protrusions so that the flow in the glass pipe 9 will not be interfered. When the protrusion structures illustrated in FIG. 11 are adopted for the trap wire, too, the same effect as that of the spiral coil described above can be obtained.

When the trap wire 101, 101a, or 101b having a three-dimensional structure in the flow passageway direction is disposed in the glass pipe 9 as according to the present example, the following effects can be obtained in addition to the effects of the foregoing examples.

First, when the trap wire 101, which is a kind of obstacle, is disposed in the glass pipe 9, the length of time for which the fine particles as the object of examination stay in the glass pipe 9 is extended, whereby the efficiency of vaporization of the fine particles by heating by the infrared lamp 8e can be increased.

Secondly, because the trap wires 101, 101a, and 101b are structures which are three-dimensional in the flow passageway direction, clogging such as may occur in the case of conventional technology is not caused.

When the fine particles as the object of detection are made of a material with a low rate of absorption with respect to the wavelength range of the infrared lamp 8e, or when the light-receiving area of the fine particles themselves is small, vaporization of the fine particles by heating inside the glass pipe 9 may not be sufficiently promoted. In such a case, the problem can be solved by increasing the amount of irradiation of infrared ray onto the fine particles as the object of detection.

When trap wire 101 or the like having a three-dimensional structure in the flow passageway direction as described in the present example is used, the explosive material fine particles 12 as they enter the glass pipe 9 contact or become temporarily attached to the trap wire 101 and the like. As a result, the explosive material fine particles 12 as the object of detection remain longer within the range of irradiation with infrared ray, whereby the amount of irradiation of infrared ray onto the fine particles can be increased, promoting the vaporization by heating. In addition, because the trap wire 101 has the three-dimensional structure in the flow passageway direction, clogging is not caused structurally, preventing the problem of a decrease in throughput, for example.

The material of the trap wire 101 may be selected depending on the characteristics of the fine particles as the object of analysis. When the explosive material fine particles 12 such as TNT are the object of detection, the trap wire 101 may be formed of a metal such as stainless steel. In this case, the trap wire 101 itself can be heated by the infrared lamp 8e. Namely, the metal trap wire 101 is disposed in the glass pipe 9, so that the explosive material fine particles 12 as they come into contact with the heated trap wire 101 are directly heated and vaporized. Thus, compared with the case of vaporizing the fine particles by heating only with the radiation heat from the infrared lamp 8e, the fine particles can be efficiently vaporized.

When the trap wire 101 can be made of a metal, such as stainless steel, or a material that can be heated with the radiation heat from the infrared lamp 8e, the heating source and the heating member may be separated, whereby the environment for vaporizing the fine particles can be separated from the external environment. As a result, the influence of disturbance depending on the environment and the like can be minimized, enabling accurate detection.

Sixth Example

Another configuration example of the fine particle detection device 100 will be described. In the fifth example, the trap wire 101 having a three-dimensional structure in the flow passageway direction is disposed inside the glass pipe 9, and the fine particles and the like are caused to become attached to the trap wire 101, thereby extending the time of heating of the fine particles. However, the attachment of the fine particles and the like onto the trap wire 101 is passive, as it is based on the Brownian motion of the fine particles. In the present example, a mechanism is adopted whereby the fine particles and the like are caused to actively become attached to the wire trap having a three-dimensional structure in the flow passageway direction.

Figure 12:
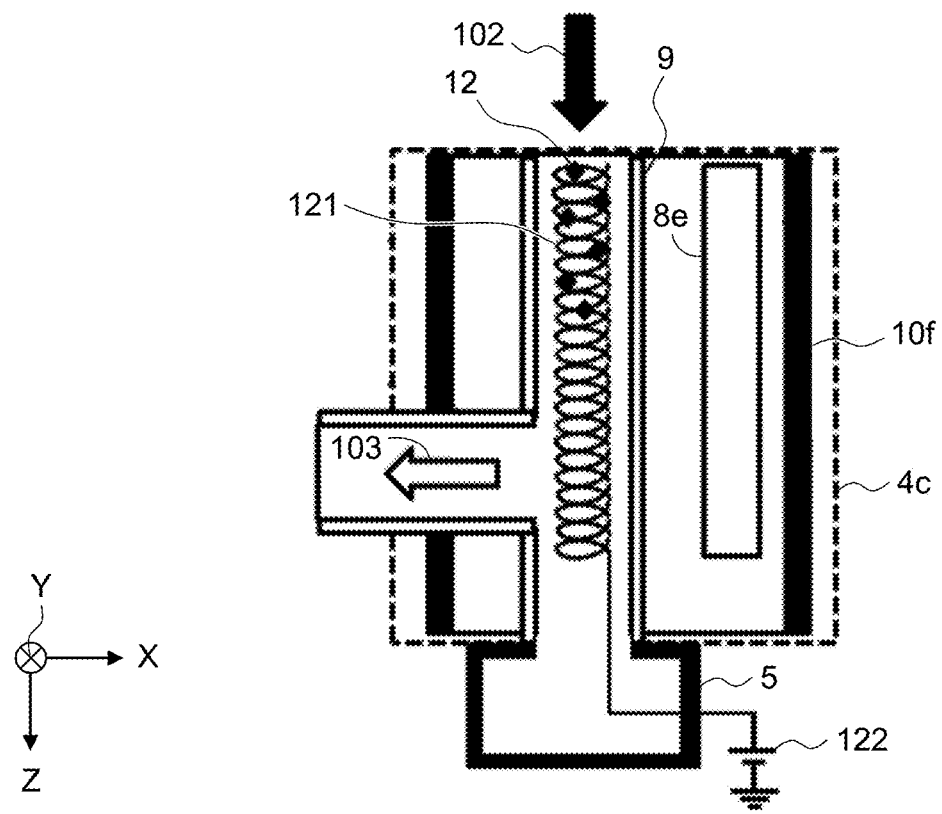
FIG. 12 illustrates another configuration example of the heating vaporization unit which may be preferably used in the fine particle detection device.

FIG. 12 illustrates a configuration example of a heating vaporization device 4c used in the present example. In FIG. 12, portions corresponding to those of FIG. 10 are designated with the same or corresponding signs. The configuration of the present example is similar to the fine particle detection device 100 according to the fifth example with the exception of the heating vaporization device 4c. Thus, detailed description of elements other than the heating vaporization device 4c will be omitted.

In the case of the present example, inside the glass pipe 9 of the heating vaporization device 4c, there is installed a charged-type trap wire 121 having a three-dimensional structure in the flow passageway direction. The charged-type trap wire 121 is connected to a power supply 122 via a power feeding line, and is positively or negatively charged. The explosive material fine particles 12 as they pass inside the glass pipe 9 partially or entirely become adsorbed on the charged-type trap wire 121 by charging, and are immobilized thereon.

In the present example too, the infrared ray radiated from the infrared lamp 8e is condensed within the glass pipe 9 by the reflecting mirror 10f with the reflecting surface having an elliptical or semi-elliptical shape or an approximate shape thereof. Thus, the explosive material fine particles 12 that are passing inside the glass pipe 9 or that has become adsorbed on the charged-type trap wire 121 by charging are partially or entirely vaporized by heating, generating the vapor component 13. The vapor component 13, as described above with reference to FIG. 3, is guided via the intake pipe 17 to the analysis device 1 (not illustrated), where, if the vapor component 13 is derived from explosive material fine particles, the explosive substance is identified.

When the charged-type trap wire 121 has the positively or negatively charged configuration as in the fine particle detection device 100 according to the present example, the following effects can be provided in addition to the effects obtained by the foregoing examples.

First, because the fine particles as the object of examination are immobilized on the charged-type trap wire 121 by charged adsorption, the length of time for which the fine particles remain in the heating region inside the glass pipe 9 can be extended. As a result, the efficiency of vaporization by the radiation heat emitted from the infrared lamp 8e can be increased.

Second, because the fine particle residue is immobilized on the charged-type trap wire 121 by charged adsorption, the vapor component and the fine particle residue can be separated with increased efficiency.

Seventh Example

Another configuration example of the fine particle detection device 100 will be described. In the fifth and sixth examples, the trap wire 101 having a three-dimensional structure in the flow passageway direction is installed inside the glass pipe 9, and the fine particles and the like are caused to become attached to the trap wire 101, whereby the length of time for which the fine particles are heated by the infrared ray is increased, promoting vaporization.

In the heating vaporization device according to the present example too, a trap wire having a three-dimensional structure in the flow passageway direction is used so as to cause the fine particles to become attached and to thereby increase the heating time. However, in the present example, the trap wire itself is used as a heat generating member.

Figure 13:
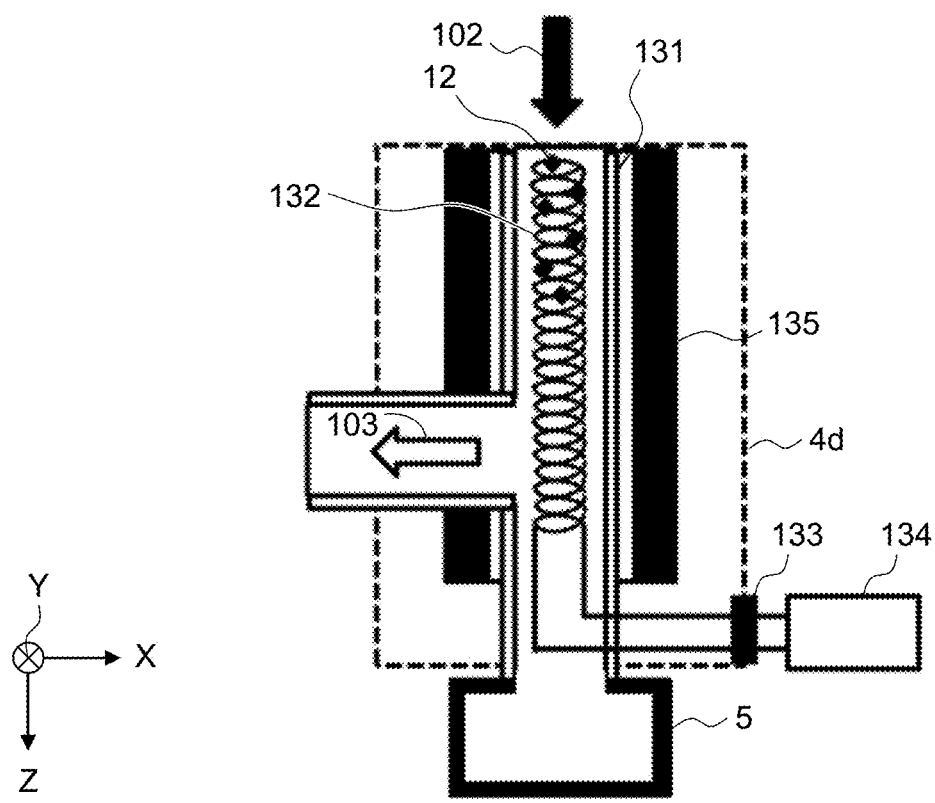
FIG. 13 illustrates another configuration example of the heating vaporization unit which may be preferably used in the fine particle detection device.

FIG. 13 illustrates a configuration example of a heating vaporization device 4d used in the fine particle detection device 100 according to the present example. In FIG. 13, portions corresponding to those of FIG. 10 are designated with the same or corresponding signs. The configuration of the present example is similar to the fine particle detection device 100 according to the fifth example with the exception of the heating vaporization device 4d. Thus, detailed description of the elements other than the heating vaporization device 4d will be omitted.

In the heating vaporization device 4d according to the present example, a heating vaporization pipe 131 is used instead of the glass pipe 9. The heating vaporization pipe 131 has the same shape as the glass pipe 9. Namely, one end of the heating vaporization pipe 131 is branched to two flow passageways corresponding to the intake pipe 17 and the branch pipe 18. The two flow passageways are connected to the analysis device 1 or the trap 5.

As mentioned above, in the present example, the trap wire itself is used as the heating member. Thus, the heating vaporization pipe 131 need not have the function of transmitting infrared ray or ultraviolet ray. Namely, the heating vaporization pipe 131 is not necessarily required to be a glass pipe.

Inside the heating vaporization pipe 131, there is disposed a heating-type trap wire 132 having a three-dimensional structure in the flow passageway direction and configured to generate heat by itself. The heating-type trap wire 132 is connected to an external heating power supply 134 via a connector 133. In order to decrease the external dissipation of heat from the heating vaporization pipe 131, a heat insulating material 135 is disposed around the heating vaporization pipe 131 so as to block dissipation of heat to the external space.

In the present example too, the heating-type trap wire 132 has a spiral structure. The material of the heating-type trap wire 132 is not limited as long as the wire can function as a heat generating member. For example, the heating-type trap wire 132 is made of a resistive heating material. As a material of this type, an inexpensive heat generating material, such as nichrome wire, may be used. Preferably, in order to suppress the outgas generated as a result of heat generation, a ceramic-coated wire heater, or a sheathed heater covered with a stainless tube and the like may be used for the heating-type trap wire 132.

When the heating-type trap wire 132 is adopted, the fine particle detection device 100 according to the present example can provide the following effects in addition to the effects obtained by the foregoing examples.

First, because the trap wire itself is a heat generating member, the fine particles coming into contact can be directly vaporized by heating. Thus, vaporization by heating can be efficiently effected compared with the foregoing examples.

Second, because a resistive heating member can be used as the trap wire, an inexpensive configuration can be adopted including a heating power supply.

Third, even in the initial state or when there is a concern for contamination by a deposit of fine particle residue, the fine particle residue can be baked out by heating the heating-type trap wire 132 to a temperature higher by 100° C. to 200° C. than a preferred temperature for vaporization of the fine particles. By performing the bake-out in the initial state, outgas can be emitted from the heater as the heating-type trap wire 132 in advance, whereby the influence of the gas emitted in the preferred temperature range for vaporizing the fine particles by heating can be decreased. Further, when there is the concern for contamination by a deposit of fine particle residue, the fine particle residue can be thermally decomposed and eliminated by the bake-out, whereby a cleaning effect can be obtained.

Eighth Example

Another configuration example of the fine particle detection device 100 will be described. In the seventh example, only one heating-type trap wire 132 having a three-dimensional structure in the flow passageway direction is disposed in the flow passageway. In the present example, a plurality of heating-type trap wires of this type is disposed in the flow passageway.

Figure 14:
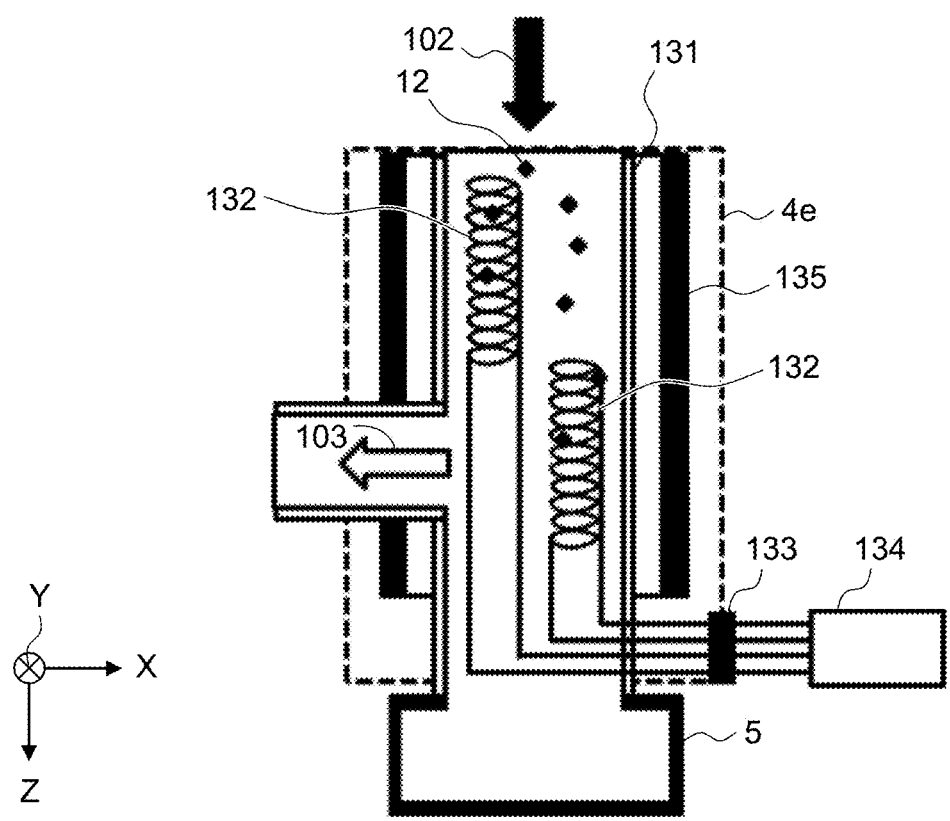
FIG. 14 illustrates another configuration example of the heating vaporization unit which may be preferably used in the fine particle detection device.

FIG. 14 illustrates a configuration example of a heating vaporization device 4e used in the fine particle detection device 100 according to the present example. In FIG. 14, portions corresponding to FIG. 13 are designated with the same or corresponding signs. The configuration of the present example is similar to the fine particle detection device 100 according to the seventh example with the exception of the heating vaporization device 4e. Thus, detailed description of the elements other than the heating vaporization device 4e will be omitted.

In the case of the heating vaporization device 4e illustrated in FIG. 14, in the heating vaporization pipe 131, there are disposed two heating-type trap wires 132 each having a three-dimensional structure in the flow passageway direction and configured to generate heat by itself. In the present example too, the heating-type trap wires 132 have a spiral structure. The heating-type trap wires 132 are connected to the external heating power supply 134 via the connector 133.

The heating-type trap wires 132 are configured to each independently manage temperature. In the case of the present example, the two heating-type trap wires 132 are set for different temperatures. Thus, the two heating-type trap wires 132 can vaporize the explosive material fine particles by heating under different conditions.

Further, in the case of the present example, the two heating-type trap wires 132 are disposed at different positions with respect to the flow passageway direction. The temperature of the heating-type trap wire 132 closer to the introduction opening for the fine particles is set relatively low, while the temperature of the heating-type trap wire 132 farther from the introduction opening for the fine particles is set relatively high. By relatively lowering the temperature on the upstream side of the flow passageway, vaporization reaction can be caused to proceed in sequence from substance having lower vaporization temperature. When the temperature setting on the upstream side of the flow passageway is high, not only will various substances be vaporized at once, but also the substances themselves may be eliminated by thermal decomposition, depending on the set temperature and the characteristics of the substances.

Thus, when a plurality of heating-type trap wires 132 is disposed inside the heating vaporization pipe 131, the fine particle detection device 100 according to the present example can provide the following effects in addition to the effects obtained by the foregoing examples.

First, because the plurality of heating-type trap wires 132 can be heated under different heating conditions, a plurality of fine particles having different vaporization temperatures can be simultaneously vaporized by heating.

Second, because the plurality of heating-type trap wires 132 is disposed, even if abnormality is caused in any of the heating-type trap wires 132 during operation, the operation can be continued by using the other heating-type trap wires 132 capable of normal operation. Thus, the maintenance period for the fine particle detection device 100 can be extended.

Ninth Example

In the present example, an example of drive operation of the infrared lamp or the ultraviolet lamp of the heating vaporization devices according to the first and the third to the sixth examples will be described.

Figure 15:
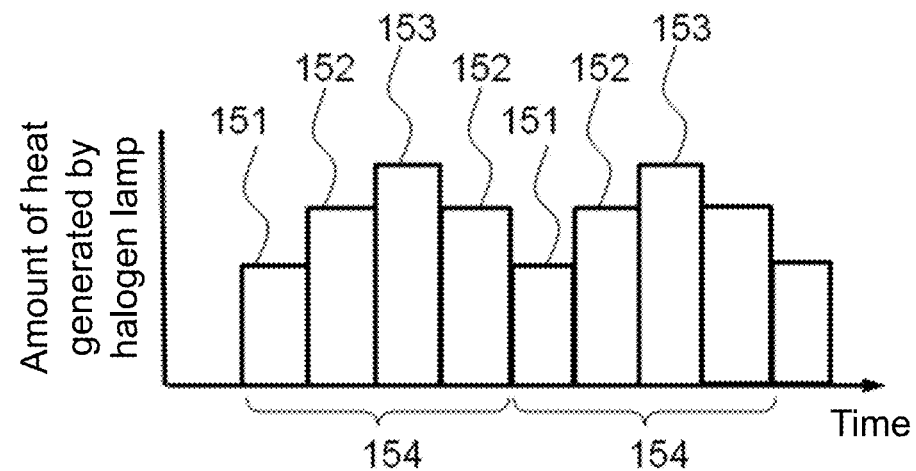
FIG. 15 illustrates an example of a radiation pattern of an infrared lamp or an ultraviolet lamp.
Figure 16:
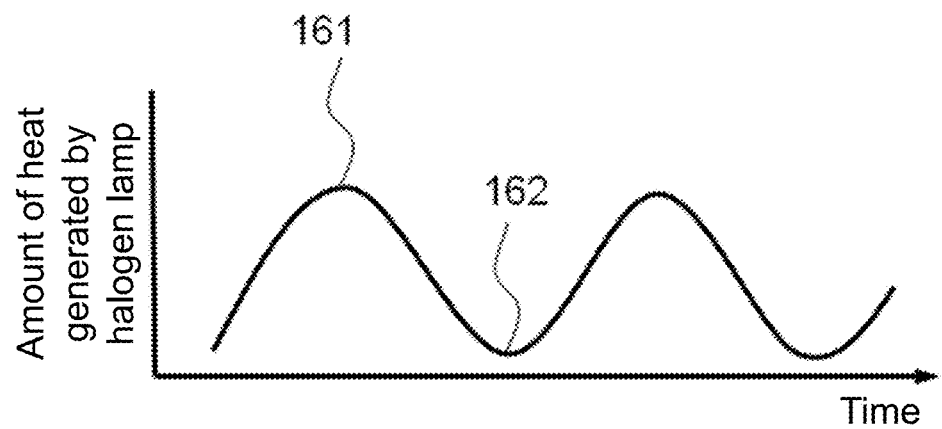
FIG. 16 illustrates an example of a radiation pattern of an infrared lamp or an ultraviolet lamp.

FIG. 15 and FIG. 16 show the radiation pattern of an infrared lamp or an ultraviolet lamp. The infrared lamp or the ultraviolet lamp is capable of rapid temperature increase/decrease. In the present example, with reference to a halogen lamp, an example of a preferred radiation pattern for use in vaporizing the explosive material fine particles by heating will be described in terms of a generated heat amount pattern.

The halogen lamp includes a tungsten filament with small thermal capacity as a heat generating member, and is capable of increasing or decreasing temperature contactlessly and at high speed. Thus, the halogen lamp is a lamp heater capable of implementing a complex heating program.

In FIG. 15, the horizontal axis shows time, and the vertical axis shows the amount of generated heat of the halogen lamp. FIG. 15 shows a radiation pattern 154 such that three amounts of generated heat 151, 152, and 153 are switched in a pulsed manner in a short time. By repeating the heat generating pattern 154 a number of times in a short time (such as on the order of several seconds), even when one halogen lamp is used, three kinds of explosive material fine particles can be substantially simultaneously vaporized by heating. For example, in the figure, the amount of generated heat 151 corresponds to a preferred heating condition for vaporizing TNT by heating; the amount of generated heat 152 corresponds to a preferred heating condition for vaporizing TATP by heating; and the amount of generated heat 153 corresponds to a preferred heating condition for vaporizing RDX by heating.

In FIG. 16, the horizontal axis shows time, and the vertical axis shows the amount of generated heat of the halogen lamp. FIG. 16 shows a radiation pattern such that the amount of generated heat is continuously changed. In FIG. 16, the radiation pattern is a sine wave having the period on the order of several seconds. For example, an upper limit 161 of the amount of generated heat of the halogen lamp represents a preferred heating condition for vaporizing RDX by heating; and a lower limit 162 of the amount of generated heat of the halogen lamp represents a preferred heating condition for vaporizing TNT by heating. In this case, a plurality of explosive material fine particles having preferred heating conditions in the temperature range between the upper and lower limits can be substantially simultaneously vaporized by heating.

As described above, when the amount of generated heat of the halogen lamp is changed by either heat generating pattern, a plurality of heating conditions can be realized in a simulated manner using one halogen lamp. Thus, more kinds of explosive material fine particles can be vaporized by heating using one halogen lamp.

In the present example, an example has been described in which the heat generating pattern is a sine wave. Obviously, however, the heat generating pattern may include a triangular wave or a trapezoidal wave, for example.

Tenth Example

While the representative examples of the present invention have been described along the spirit of the present invention, the present invention is not limited to the forgoing examples, and various other embodiments may be possible within the spirit of the present invention. For example, other elements may be incorporated in the examples, or some of the elements of the examples may be deleted or replaced with other elements. One example may be combined with another example.

In the foregoing examples, the case is contemplated in which the fine particles as the object of detection are separated from a medium having the authentication function, such as an IC card. However, the invention may be applied to cases where the fine particles are separated or trapped from an admission card, a ticket, a transit pass, a commuter pass, baggage, clothing, human body, vehicle-interior equipment (such as the electronic toll collection (ETC) system card), or foods.

REFERENCE SIGNS LIST

1 Analysis device
2 Fine particle processing device
3 Fine particle trap device
4, 4a, 4b, 4c, 4d, 4e Heating vaporization device
5 Trap
6 Fine particle collection unit
7 Cyclone centrifugal separator
8, 8a, 8b, 8c, 8d, 8e Infrared lamp
9 Glass pipe
10, 10a, 10b, 10c, 10d, 10e, 10f Reflecting mirror
11, 11a, 11b, 11c, 11d Infrared lamp control device
12, 12a Explosive material fine particles
13 Vapor component
14 Fine particle residue
15 Trajectory of vapor component 13
16 Trajectory of explosive material fine particles 12 that have been separated and concentrated, and residue 14 of the fine particles that have not been vaporized by heating vaporization unit
17 Intake pipe
18 Branch pipe
19 Arrow
41 Security gate
42 Card reader
43 Separating mechanism
44 Trap device
45 Open/close gate
46 Object of examination
47 ID card
48 Proximity sensor
49 Compressed air spray nozzle
50 Axial-flow fan
51 Fan control device
52 Detection control device
71 Coupling pipe
72 Centrifugal separator
73 Intake pipe
74 Arrow
75 Wall surface heater
76 Arrow
77 Arrow
100 Fine particle detection device
101 Trap wire
102 Arrow indicating direction of travel of explosive material fine particles 12
103 Arrow indicating direction of flow of vapor component 13
121 Charged-type trap wire
122 Power supply
131 Heating vaporization pipe
132 Heating-type trap wire
133 Connector
134 Heating power supply
135 Heat insulating material
151 First amount of generated heat
152 Second amount of generated heat
153 Third amount of generated heat
154 Heat generating pattern of halogen lamp
161 Upper limit of the amount of generated heat of the halogen lamp
162 Lower limit of the amount of generated heat of the halogen lamp

The invention claimed is:

1. A fine particle detection device comprising:
a trap device that traps fine particles;
a vaporization device that vaporizes the fine particles trapped by the trap device by vaporization or decomposition;
a first flow passageway, that is downstream of and separate from the vaporization device, in which a mixture of a component vaporized by the vaporization device and a residual component that has not been vaporized by the vaporization device flows;
a second flow passageway branching from the first flow passageway in a direction of inertial force acting on the residual component, the residual component being introduced into the second flow passageway;
a third flow passageway branching from the first flow passageway in a direction different from the direction of the inertial force, the vaporized component being introduced into the third flow passageway; and
an analysis device that analyzes a component introduced into the third flow passageway, wherein
the vaporization device is a light reflecting vaporization device.

2. The fine particle detection device according to claim 1, wherein the vaporization device includes
a light source that radiates an infrared ray and/or an ultraviolet ray; and
a reflecting mirror that condenses the infrared ray and/or the ultraviolet ray radiated from the light source onto the first flow passageway made of a material transmitting the infrared ray and/or the ultraviolet ray.

3. The fine particle detection device according to claim 1, wherein the vaporization device includes
a plurality of light sources that radiate an infrared ray and/or an ultraviolet ray; and
a reflecting mirror that condenses the infrared ray and/or the ultraviolet ray radiated from the plurality of light sources onto one first flow passageway made of a material that transmits the infrared ray and/or the ultraviolet ray.

4. The fine particle detection device according to claim 2, wherein the vaporization device includes an obstacle disposed in the first flow passageway and having a three-dimensional structure in the direction of the flow passageway.

5. The fine particle detection device according to claim 1, wherein the vaporization device includes a heating source disposed in the first flow passageway and having a three-dimensional structure in the direction of the flow passageway.

6. The fine particle detection device according to claim 2, wherein:
the reflecting mirror has an elliptical or semi-elliptical shape or an approximate shape thereof; and
the light source is disposed at one focal point position and the first flow passageway is disposed at the other focal point.

7. The fine particle detection device according to claim 3, wherein:
the reflecting mirror has an elliptical or semi-elliptical shape or an approximate shape thereof; and
the light source is disposed at one focal point position and the first flow passageway is disposed at the other focal point.

8. The fine particle detection device according to claim 2, wherein the light source changes the amount of radiation over time in a pulsed or continuous manner.

9. The fine particle detection device according to claim 3, wherein the light source changes the amount of radiation over time in a pulsed or continuous manner.

10. The fine particle detection device according to claim 3, wherein the plurality of light sources include any of a near-infrared ray, a mid-infrared ray, and a far-infrared ray, or a combination thereof.

11. The fine particle detection device according to claim 5, wherein:
a plurality of the heating sources are disposed in the first flow passageway; and
the plurality of heating sources are used under mutually different heating conditions.

12. The fine particle detection device according to claim 11, wherein, of the plurality of heating sources, the heating source disposed on an upstream side is used at a lower temperature than the heating source disposed on an downstream side.

13. The fine particle detection device according to claim 1, wherein the second flow passageway has a wall surface temperature lower than a wall surface temperature of the third flow passageway.

14. The fine particle detection device according to claim 1, wherein a mechanism for causing particle precipitation of the residual component using centrifugal force is disposed at the branch portion of the second flow passageway and the third flow passageway, and causing introduction of the residual component into the second flow passageway.

15. The fine particle detection device according to claim 4, comprising a power supply that positively or negatively charges the obstacle.

16. A security gate comprising:
a separation device that separates fine particles from an object of examination;
a trap device that traps the separated fine particles;
a vaporization device that vaporizes the fine particles trapped by the trap device by vaporization or decomposition;
a first flow passageway, that is downstream of and separate from the vaporization device, in which a mixture of a component vaporized by the vaporization device and a residual component that has not been vaporized by the vaporization device flows;
a second flow passageway branching from the first flow passageway in a direction of inertial force acting on the residual component, the residual component being introduced into the second flow passageway;
a third flow passageway branching from the first flow passageway in a direction different from the direction of the inertial force, the vaporized component being introduced into the third flow passageway;
an analysis device that analyzes a component introduced into the third flow passageway; and
a control device that controls opening or closing of a gate based on a result of analysis by the analysis device, wherein
the vaporization device is a light reflecting vaporization device.

* * * * *